(12) United States Patent
Gusev

(10) Patent No.: US 7,817,270 B2
(45) Date of Patent: Oct. 19, 2010

(54) NANOSECOND FLASH PHOTOLYSIS SYSTEM

(76) Inventor: Alex Gusev, 1748 Independence Blvd., Suite G-6, Sarasota, FL (US) 34234

( * ) Notice: Subject to any disclaimer, the term of this patent is extended or adjusted under 35 U.S.C. 154(b) by 196 days.

(21) Appl. No.: 12/019,678

(22) Filed: Jan. 25, 2008

(65) Prior Publication Data

US 2008/0186486 A1    Aug. 7, 2008

Related U.S. Application Data

(60) Provisional application No. 60/888,142, filed on Feb. 5, 2007.

(51) Int. Cl.
*G01J 3/30* (2006.01)
(52) U.S. Cl. ...................................... 356/318
(58) Field of Classification Search .................. 356/318
See application file for complete search history.

(56) References Cited

U.S. PATENT DOCUMENTS

| 5,706,094 A * | 1/1998 | Maris .......................... 356/432 |
| 7,106,971 B1 * | 9/2006 | Davis .......................... 398/125 |
| 2003/0055342 A1 * | 3/2003 | Toida .......................... 600/478 |
| 2005/0036150 A1 * | 2/2005 | Izatt et al. .................... 356/479 |

* cited by examiner

*Primary Examiner*—Tarifur Chowdhury
*Assistant Examiner*—Abdullahi Nur
(74) *Attorney, Agent, or Firm*—Fraser Clemens Martin & Miller LLC; Donald R. Fraser

(57) ABSTRACT

A nanosecond pump-probe LFP system is disclosed and adapted to a substantially lower energy requirement of a pump light source and to electronically extend a time interval during which a chemical change of a sample may be measured. The LFP system includes a photonic crystal fiber based probe light source, a pump light source adapted to produce light pulses with microjoule or higher energy, a delay generator, computer, and a detector.

4 Claims, 1 Drawing Sheet

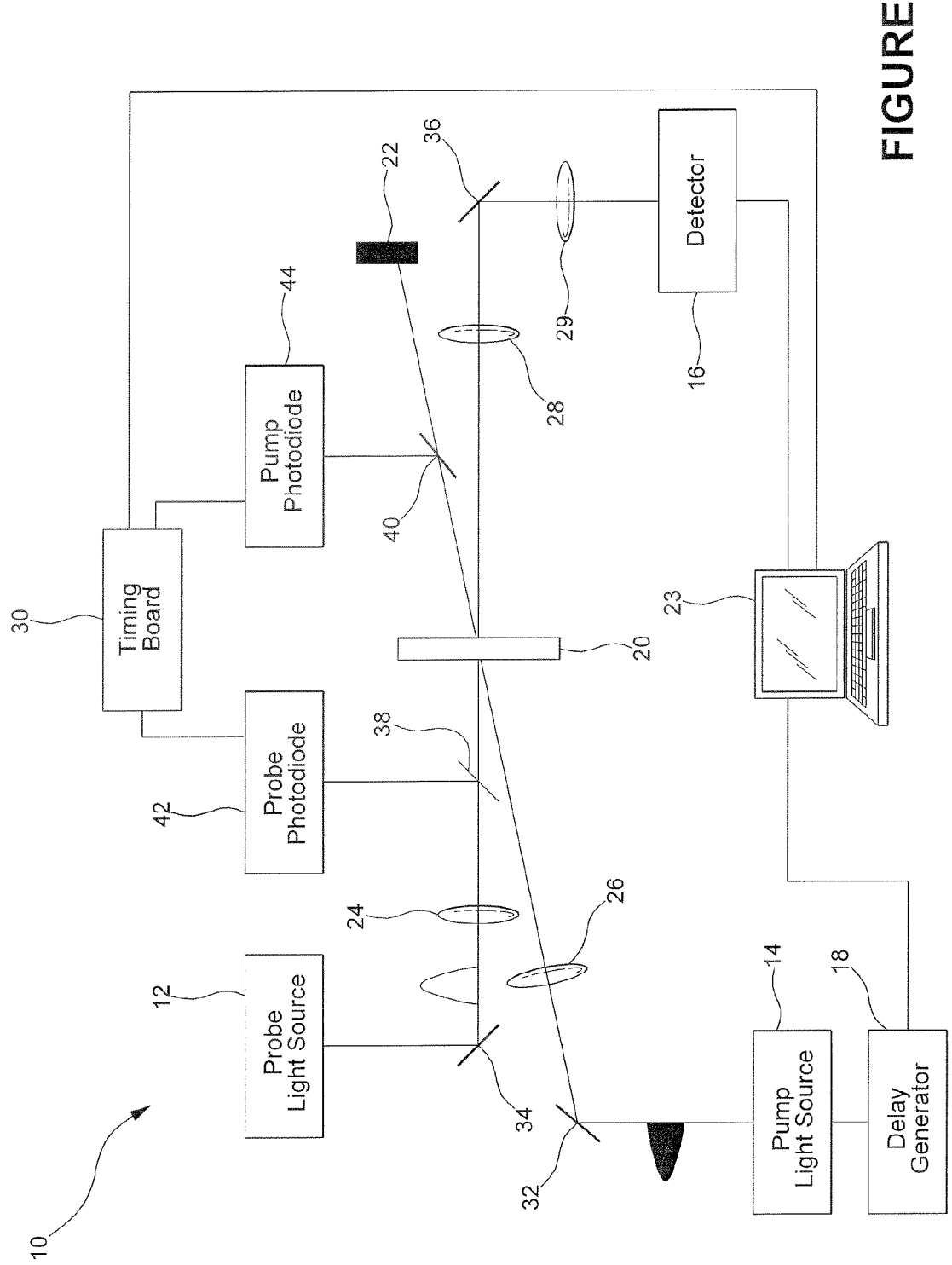
FIGURE

NANOSECOND FLASH PHOTOLYSIS SYSTEM

CROSS-REFERENCE TO RELATED APPLICATION

This application claims the benefit of U.S. provisional patent application Ser. No. 60/888,142 filed Feb. 5, 2007.

BACKGROUND OF THE INVENTION

1. Field of the Invention

The present invention relates to the field of laser flash photolysis and more particularly to a flash photolysis system with improved performance over existing flash photolysis spectrometers.

2. Description of the Prior Art

Laser flash photolysis (LFP) is a technique utilized to study reaction mechanisms in chemical and biological processes. The technique was introduced in 1966 by Lindqvist at the CNRS in France and the technique was quickly developed by various research groups around the world. LFP was brought about by the invention of the laser, in the early 1960s. The technique of LFP consists of a pulsed laser source that generates a chemical species in a sample to be studied, an optical and electronic system capable of sensing optical changes in a sample, and a computer suitably equipped to selectively capture, process, and display the data. The optical and electronic systems constitute a fast spectrometer capable of acquiring spectra of short-lived chemical species called "intermediates". The optical and electronic systems then record the evolution of the intermediates over time. The time resolution in such fast spectrometer can be achieved by two primary methods.

A first method includes use of fast electronics where a readout of a fast detector is digitized and recorded in real time, or when an electronic gating is applied to the detector. The electronic gating is typically used with array-based spectrometers where the output cannot be processed rapidly enough to perform real time data acquisition. Both techniques typically utilize continuous wave (CW) or pulsed xenon arc lamps as a probe light source. Due to the low intrinsic brightness and poor collimation of a probe beam produced by the probe light source, an optical overlap between the probe and a pump (excitation) beam takes place over an area of approximately 1 cm$^2$, thereby placing energy requirements on the laser pulse necessary to induce chemical changes in the sample. The corresponding pump laser pulses typically have energy of a few millijoules. Because of the pulse energy requirement, only a limited number of lasers, known as Q-switched lasers, can be used with the xenon arc lamp probe light source to produce the required energy.

A second method is called optical gating or the "pump-probe" method. In this method, the dynamics of a chemical change of a sample is monitored by studying a series of light pulses from a laser at different times as the light pulses (pump beam) are passed through the sample. The probe and pump beams travel trough the same volume of the sample studied. A pulse of the pump beam induces a transient chemical change in the sample which affects the optical properties of the sample. A spectrum of a pulse of the probe beam passing through the sample is altered by the changes made to the sample by the pump beam depending on when the probe pulse arrives at the sample with respect to the pump pulse.

Where the probe beam travels in front of the pump beam, the probe beam will only measure the sample before the excitation event. As the probe beam is delayed, it arrives at the sample simultaneously with the pump pulse, corresponding to a time zero. The delay of the probe beam is incrementally increased over a desired time interval. The corresponding changes in the probe beam monitored by a detector are therefore assigned to particular delays (time) after the excitation event. A series of probe beams at various delays represents information about the dynamics of the changes in the sample caused by the pump beam.

At each of the delays of the probe beam, two spectra of the probe beam are recorded by the detector. A first spectrum corresponds to the probe beam traveling through the sample together with the pump beam. A second spectrum, a reference spectrum, corresponds to the probe beam sent through the sample without the pump beam. Usually at a particular pump probe delay, a series of such probe spectrum pairs are averaged in order to obtain a sufficient signal to noise ratio. The pump beam energy in such experimental setups is often limited to several microjoules. Therefore, in order to achieve comparable instrument sensitivity and similar photon flux in the excitation beam, the pump beam and the probe beam are spatially overlapped in the sample over an area less than 1 mm$^2$. Generation of a probe beam that can satisfy the above requirement is possible only if a highly collimated beam such as a laser is used.

Optical gating has been successfully used with femtosecond and picosecond lasers. The femtosecond or picosecond laser output is split into several parts, one of which is used to produce a probe beam with desired wavelength specifications, usually through super-continuum generation or optical parametric amplification. The resulting beam is then used to probe the photo-induced changes in the sample. The time resolution is realized by varying the travel path length of the probe beam with respect to the pump beam, which allows for extremely high temporal resolution, down to several femtoseconds. However, the longest practical time scale in this case is limited to several nanoseconds. Expansion of the time scale in such experimental conditions is rather complicated and requires introduction of an expensive laser system and a larger amount of space for the equipment, such as 8-10 ft$^2$.

SUMMARY OF THE INVENTION

A LFP system and method of laser flash photolysis have been surprisingly developed and are adapted to substantially lower the energy requirement of a pump light source and to extend a time interval for which a chemical change and detection of the change of a sample may be measured. The LFP system includes a probe light source, a pump light source adapted to produce light pulses with microjoule or higher level energy, a delay generator, and a detector.

The invention also provides methods of laser flash photolysis.

One method comprises the steps of producing a first pulsed beam of light; directing the first pulsed beam of light through a sample; producing a second pulsed beam of light caused to travel through the sample and initiate a chemical reaction in the sample; regulating a time delay between the pump light source pulsed beam of light and the probe light source pulsed beam of light; detecting the first pulsed beam of light exiting the sample; and detecting a change in absorption of the first pulsed beam of light in the sample caused by the second pulsed beam of light.

BRIEF DESCRIPTION OF THE DRAWINGS

The above and other objects and advantages of the invention will become readily apparent to those skilled in the art from reading the following detailed description of the invention when considered in the light of the accompanying drawing which is a schematic layout of an LFP system according to an embodiment of the present invention.

DETAILED DESCRIPTION OF THE PREFERRED EMBODIMENTS OF THE INVENTION

Referring to the FIGURE, there is illustrated a LFP system 10 which includes a probe light source 12, a pump light source 14, a detector 16, and a delay generator 18.

The probe light source 12 shown is a photonic crystal fiber pumped by an appropriate laser. The probe light source 12 is adapted to be focused to areas as small as several square microns. It is understood that the probe light source 12 may be any conventional probe light source that is adapted to be focused to areas as small as several square microns such as a Q-switched sub-nanosecond microchip pulsed laser coupled to a photonic fiber, for example.

The pump light source 14 is typically a laser adapted to produce a collimated beam with an energy level of at least several microjoules and referred to as an excitation light source. The pump light source 14 may be an amplified femtosecond laser, a picosecond laser, a Q-switched nanosecond laser, a dye laser, a nitrogen laser, or a nanosecond microchip laser, as desired.

The detector 16 is a broadband detector, such as a CCD based spectrometer adapted to measure a change in the absorption of light by a sample 20. The detector 16 may be further adapted to transmit a measurement signal to a computer 23. It is understood that the detector 16 may be any device adapted to measure the properties of light over a specific portion of the electromagnetic spectrum.

The delay generator 18 is typically a digital delay generator. The delay generator 18 is in electrical communication with the computer 23 and adapted to electronically control the time delay between the probe beam produced by the probe light source 12 and the pump beam produced by the pump light source 14. The delay generator 18 is further adapted to selectively vary the delay between the pump beam and the probe beam by any amount, though typical LFP experimentation rarely requires a delay of over 1 second.

The LFP system 10 further includes a beam block 22, a plurality of lens optics 24, 26, 28, 29, a timing board 30, a plurality of reflective optics 32, 34, 36, a plurality of beam splitters 38, 40, and a plurality of photodiodes 42, 44.

The beam block 22 is adapted to capture and absorb electromagnetic energy such as, a beam of collimated light.

The lens optics 24, 26, 28, 29 includes a first lens 24, a second lens 26, a third lens 28, and a fourth lens 29. The first lens 24 is disposed in the path of the beam produced by the probe light source 12 and is adapted to focus the probe beam into the sample 20. The second lens 26 is disposed in the path of the beam produced by the pump light source 14 and is adapted to focus the pump beam into the sample 20. The third lens 28 and the fourth lens 29 are adapted to collect and guide the beam produced by the probe light source 12 to the detector 16. Although the LFP system 10 is shown having four lens optics 24, 26, 28, 29, it is understood that any number of lens optics may be used, as desired.

The reflective optics 32, 34, 36, may be any conventional reflective optics to direct light beams such as mirrors, for example. The reflective optics 32, 34, 36 are disposed in the path of the beams generated by the probe light source 12 and the pump light source 14 to affect the desired direction of the beams. Although the LFP system 10 is shown having three reflective optics 32, 34, 36, it is understood that any number of reflective optics may be used to affect the desired direction of the beams.

The beam splitters 38, 40 include a first beam splitter 38 and a second beam splitter 40. The first beam splitter 38 is disposed in the path of the beam generated by the probe light source 12 to reflect at least a portion of the beams in a desired direction. The second beam splitter 40 is disposed in the path of the beam generated by the pump light source 14 to reflect at least a portion of the beams in a desired direction.

The photodiodes 42, 44 include a first photodiode 42 and a second photodiode 44 in electrical communication with a timing board 30. The first photodiode 42, also known as the probe photodiode, is adapted to receive at least a portion of the probe beam reflected by the first beam splitter 38. The second photodiode 44, also known as the pump photodiode, is adapted to receive at least a portion of the pump beam reflected by the second beam splitter 40.

In use, the probe light source 12 generates probe beam pulses that are focused into an area of approximately 1 mm$^2$ in the sample 20 by the first lens 24 while the pump light source 14 generates pump beam pulses that are focused into the same area of approximately 1 mm$^2$ by the second lens 26 and having an energy-level of several microjoules. The probe and pump beams are therefore caused to spatially overlap in the sample 20. The pump beams are captured by a beam block 22 after passing through the sample 20. The probe beam is collected by the third lens 28 and the fourth lens 29 and guided into the detector 16. Reflective optics 32, 34, 36 are provided to direct the beams from the light sources 12, 14. Changes to the sample 20 and the difference in light absorption of the sample 20 are then measured by the detector 16 and recorded by the computer 23.

The probe beam pulse is produced at a constant frequency of approximately 5 kHz. It is understood any frequency may be used, as desired. Since the frequency of the probe beams produced by the probe light source 12 is known, the time period between adjacent probe beams may be easily calculated. For example, a 5 kHz repetition frequency has a period of 200 microseconds. The computer 23 activates the pump light source 14 through the delay generator 18. The signal to activate the pump light source 14 is sent to the pump light source 14 so that that the signal precedes the probe pulse by a desired time interval, thereby generating a desired pump-probe delay.

To determine the exact delay between the pump beam pulses and probe beam pulses as the beams are caused to travel through the sample 20, a portion of the probe beam is reflected by the first beam splitter 38 to the first photodiode 42 while a portion of the pump beam is reflected by the second beam splitter 40 to the second photodiode 44. The portion of the pump and probe beams is typically a relatively small fraction of the beams, such as 1%, for example. Signals produced by the photodiodes 42, 44 are transmitted to a counter or timing board 30 to calculate the interval between the pulses of the beams. To obtain a spectrum of the probe beam pulse without the pump beam pulse present in the sample 20, a signal is sent to the pump light source 14 at a rate of every other probe beam pulse.

By varying the timing of the probe beam and pulse beam with the delay generator 18, the delay between the pulses available for experimentation on a sample 20 by the LFP system 10 may be varied as desired, though typically the interval for experimentation will be less than one second. Additional benefits of the LFP system 10 include a reduction in the overall size of the LFP system 10 to an area of less than approximately 4 ft$^2$ by including optical components such as the lens optics 24, 26, 28, 29 and the reflective optics 32, 34, 36 to direct the beams, thereby minimizing the overall cost of the LFP system 10 as compared to other commercially available LSP systems.

From the foregoing description, one ordinarily skilled in the art can easily ascertain the essential characteristics of this invention and, without departing from the spirit and scope thereof, can make various changes and modifications to the invention to adapt it to various usages and conditions in accordance with the scope of the appended claims.

What is claimed is:

1. A system for flash photolysis comprising:
   a probe light source to generate a first pulsed beam of light to travel through a sample in a flash photolysis application, wherein the probe light source is a laser energized photonic crystal fiber;
   a pump light source to generate a second pulsed beam of light to travel through the sample and initiate a chemical reaction in the sample;
   a delay generator to regulate a time delay between generation of the first beam of light and generation of the second beam of light throughout the flash photolysis application; and
   a detector to receive the first beam of light exiting the sample to detect a change in absorption of the first beam of light in the sample caused by the second beam of light.

2. The system for flash photolysis according to claim 1, further including a timing board to calculate the time delay between the first pulsed beam of light and the second pulsed beam of light.

3. A system for flash photolysis comprising:
   a probe light source adapted to generate a first pulsed beam of light caused to travel through a sample to be tested in a flash photolysis experiment;
   a pump light source adapted to generate a second pulsed beam of light caused to travel through the sample and initiate a photochemical reaction in the sample;
   a delay generator to regulate a time delay between generation of the first beam of light and generation of the second beam of light throughout the flash photolysis experiment;
   a plurality of photodiodes;
   a beam splitter to direct a portion of the first pulsed beam of light to at least one of the photodiodes and a portion of the second pulsed beam of light to at least one of the photodiodes;
   a timing board in electrical communication with the photodiodes, to calculate the time delay between the first pulsed beam of light and the second pulsed beam of light; and
   a detector to receive the first pulsed beam of light exiting the sample to measure a spectrum of the sample before and after the photochemical reaction.

4. The system for flash photolysis according to claim 3, wherein the probe light source is a laser energized photonic crystal fiber.

* * * * *